(12) United States Patent
Nishino et al.

(10) Patent No.: US 7,569,822 B2
(45) Date of Patent: Aug. 4, 2009

(54) IMAGE INSPECTION DEVICE AND IMAGE INSPECTION METHOD USING THE IMAGE INSPECTION DEVICE

(75) Inventors: Hirohisa Nishino, Tokyo (JP); Takao Ohara, Tokyo (JP); Masahiko Uno, Tokyo (JP)

(73) Assignee: Mitsubishi Electric Corporation, Chiyoda-ku, Tokyo (JP)

( * ) Notice: Subject to any disclaimer, the term of this patent is extended or adjusted under 35 U.S.C. 154(b) by 38 days.

(21) Appl. No.: 11/785,408

(22) Filed: Apr. 17, 2007

(65) Prior Publication Data

US 2007/0257192 A1 Nov. 8, 2007

(30) Foreign Application Priority Data

May 8, 2006 (JP) ............................. 2006-129218

(51) Int. Cl.
*G01J 5/02* (2006.01)
(52) U.S. Cl. .................................... 250/341.1
(58) Field of Classification Search .............. 250/336.1, 250/338.1, 341.4, 332, 339.11, 559.45, 559.42
See application file for complete search history.

(56) References Cited

U.S. PATENT DOCUMENTS

2002/0088952 A1* 7/2002 Rao et al. ............... 250/559.45
2003/0218145 A1* 11/2003 Tanabe ................... 250/559.45

FOREIGN PATENT DOCUMENTS

JP 08-220008 A 8/1996
JP 2000-065759 A 3/2000

OTHER PUBLICATIONS

E. Rueland et al., "Optical μ-Crack Detection In Combination With Stability Testing for In-Line-Inspection of Wafers and Cells", 20th European Photovoltaic Solar Engery Conference, Jun. 6-10, 2005, Barcelona, Spain, pp. 3242-3245.

* cited by examiner

*Primary Examiner*—Christine Sung
*Assistant Examiner*—Faye Boosalis
(74) *Attorney, Agent, or Firm*—Buchanan Ingersoll & Rooney PC

(57) ABSTRACT

In an inspection of a semiconductor wafer for a defect, when infrared light passing through a semiconductor wafer is imaged by a camera and an inspection is conducted using the image, a problem that halation occurs in the camera due to light leaking from the side of the inspection object, which makes it impossible to conduct an inspection at the periphery portion occurs. An inspection object is irradiated by an infrared light source, and transmitted light is imaged by an infrared camera to be conducted. With the use of mask means that secures a clearance from the end portion on the outer side, it is possible to inspect on the peripheral portion. Also, as means for supporting the object, plural sets of those configured to be capable of evacuating are used, and by allowing the plural sets to evacuate alternately, it is possible to inspect across the entire surface.

18 Claims, 10 Drawing Sheets

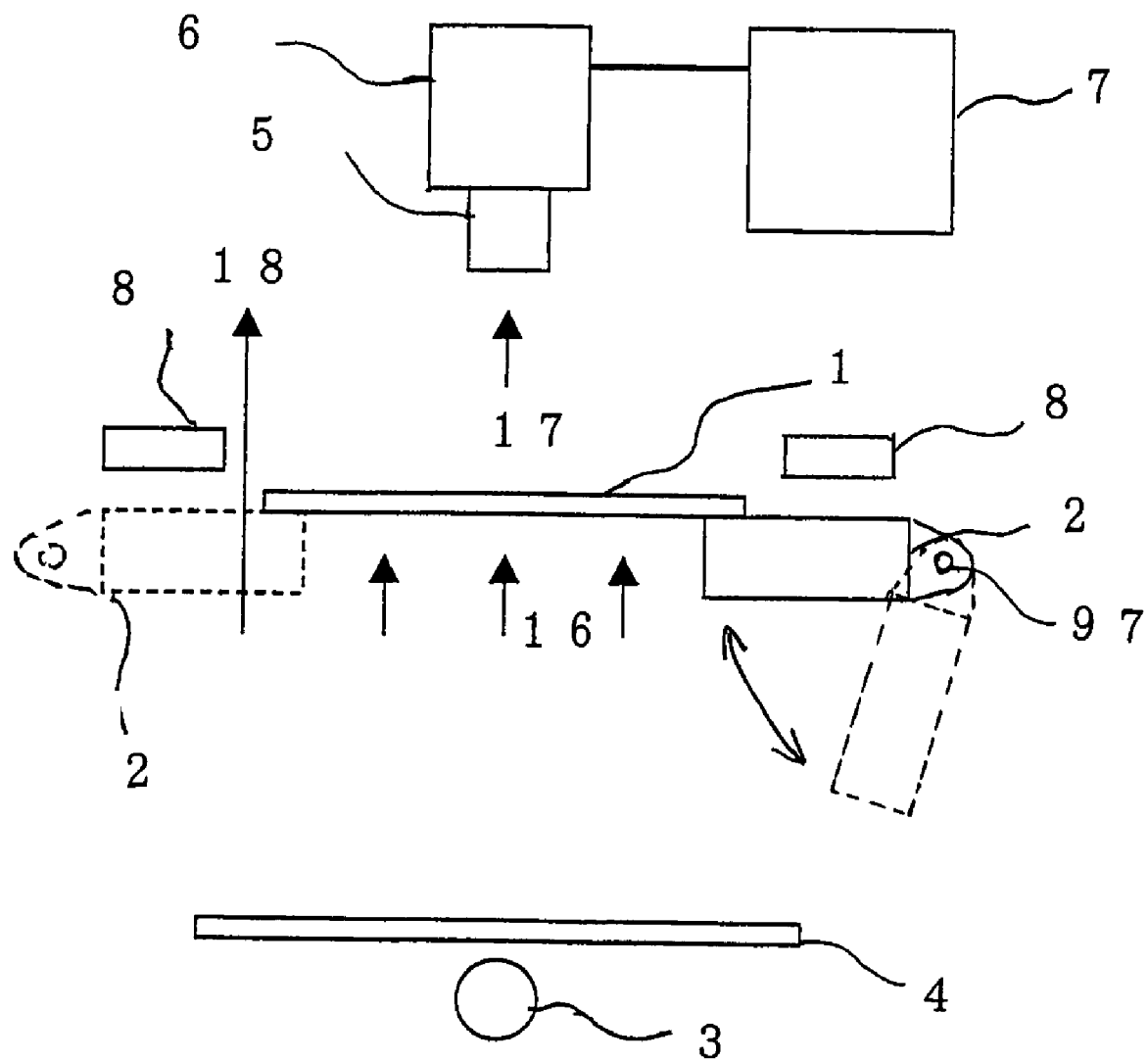
F I G. 9

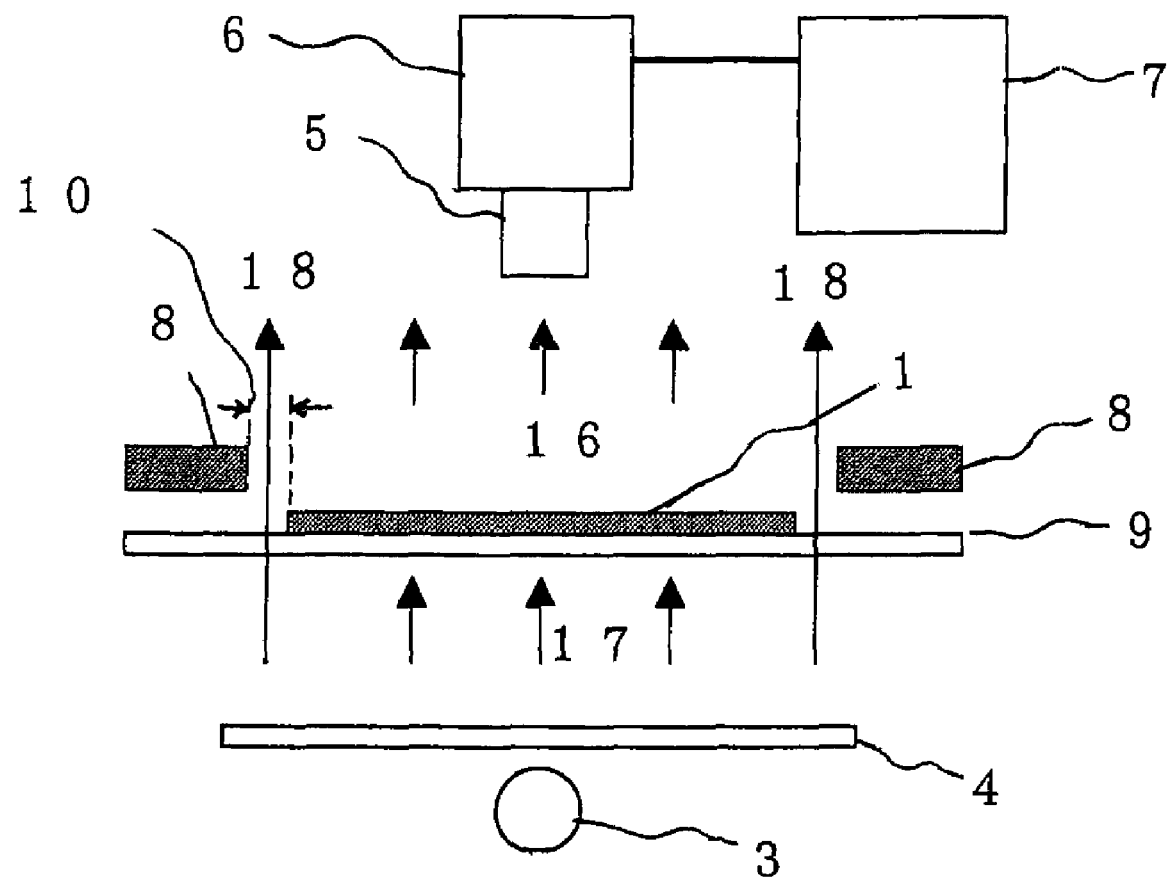
F I G. 1 0

IMAGE INSPECTION DEVICE AND IMAGE INSPECTION METHOD USING THE IMAGE INSPECTION DEVICE

BACKGROUND OF THE INVENTION

1. Field of the Invention

The present invention relates to improvements of an image inspection method and an image inspection device for inspecting an inspection object for a defect from an image by taking an image of a plate-shaped inspection object having a property of transmitting infrared rays, for example, like a semiconductor wafer, using infrared rays.

2. Description of the Related Art

There is a device that inspects a plate-shaped transparent or translucent inspection object, such as a semiconductor wafer and a liquid crystal panel, for a defect (crack or adhesion of foreign matter) using light. Herein, for ease of description, a case where the inspection object is a semiconductor wafer will be described. It should be appreciated, however, that application of the invention is not limited to a semiconductor wafer (occasionally, referred to also as a cell). For example, JP-A-8-220008 discloses an inspection device that detects a crack of a semiconductor wafer as an inspection object by irradiating infrared rays to the semiconductor wafer. In FIG. 1 of JP-A-8-220008 are shown an inspection object 1 that transmits infrared rays, a fine adjustment stand 2 that holds the inspection object 1, an infrared light source 10 that irradiates infrared rays 12 to the inspection object 1, a diffuser 11 provided in close adhesion to the infrared light source 10, and infrared rays 12 coming out from the diffuser 11. Infrared rays 32 having passed through the inspection object 1 are detected by an infrared camera 15 equipped with an infrared lens 14, and displayed in the form of an image on a monitor 16 into which a video signal from the infrared camera is inputted.

Operations of the inspection device disclosed in JP-A-8-220008 will now be described. Infrared rays emitted from the infrared light source 10 are made homogeneous by the diffuser 11 and irradiate the inspection object 1 from the back surface thereof. In this instance, the inspection object 1 is held by the fine adjustment stand 2 at the both ends (from the lower side). Irradiated infrared rays come out from the main surface of the inspection object 1, and these transmitted infrared rays are captured into the infrared camera 15 by means of the infrared lens 14. The monitor 16 then displays an output image from the infrared camera in the form of a video that can be confirmed visually. Assume that the inspection object 1 is a semiconductor wafer before processing, for example, patterning processing, is applied thereto, then, because a transmission state of infrared rays differs between a crack and the other portions, the crack can be readily detected.

The inspection device disclosed in JP-A-8-220008 inspects the inspection object 1 using transmitted infrared rays that have passed through the inspection object 1 from the back surface to the main surface. However, because light is blocked by the fine adjustment stand 2 at the peripheral portion of the cell, light is not allowed to pass through this portion, which poses a problem that an inspection cannot be conducted in this portion. Whereas a defect of a semiconductor wafer is more likely to occur in the peripheral portion, and there has been a need to inspect the peripheral portion of a semiconductor wafer as well in order to enhance the yield of semiconductor wafers.

As has been described, the image inspection method and the image inspection device in the related art are configured in such a manner that the peripheral portion of an inspection object is shielded by a device holding the inspection object. Hence, when configured to conduct an inspection using transmitted light, light is not allowed to pass through the shielded portion. This raises a problem that there is a portion where an inspection cannot be conducted. It is, however, desirable to inspect the periphery of an inspection object, which is not necessarily limited to a semiconductor wafer, in order to fully utilize the inspection object to the periphery.

SUMMARY OF THE INVENTION

The invention was devised to solve the problems discussed above and therefore has an object to obtain an image inspection method and an image inspection device for enabling an inspection of an inspection object to be conducted thoroughly to the end portion.

An image inspection method of the invention includes: a procedure to make first support means support almost horizontally a plate-shaped inspection object having a property of transmitting infrared rays; a procedure to irradiate the infrared rays to the inspection object from one surface side; a procedure to provide mask means for shielding the inspection object from the infrared rays around an outer side of the inspection object within an plane almost same as a plate surface of the inspection object; a procedure to obtain an image by imaging infrared rays having passed through the inspection object at a portion uncovered with the first support means using an infrared camera provided on the other surface of the inspection object, and inspect the image; a procedure to make second support means support the inspection object at a position different from a position of the first support means, and then move the first support means to evacuate to a position at which the inspection object is not shielded; and a procedure to obtain an image by imaging infrared rays having passed through the inspection object at a portion uncovered with the second support means using the infrared camera, and inspect the image.

Also, an image inspection device of the invention includes: an infrared light source that irradiates infrared rays to a plate-shaped inspection object having a property of transmitting infrared rays and provided almost horizontally from one surface thereof; an infrared camera provided on the other surface of the inspection object to image the infrared rays having passed through the inspection object to obtain an image thereof; mask means for shielding the inspection object from the infrared rays disposed while securing a specific clearance from an end face of the plate-shaped inspection object on an outer side of the inspection object within a plane almost same as a plate surface of the inspection object; and inspection object hold means having support means for supporting the inspection object.

According to the image inspection method and the image inspection device of the invention, because some of plural support means supporting the inspection object wafer evacuate alternately, they do not interrupt an inspection of the semiconductor wafer at the peripheral portion. By providing the mask means that secures a specific clearance from the periphery of the semiconductor wafer, no halation occurs in the camera, which enables an inspection to be conducted in a stable manner also at the peripheral portion. By using the infrared diffusing medium also as a light scatter plate, not only it is possible to prevent halation of light more readily, but it is also possible to protect the infrared light source.

The foregoing and other object, features, aspects and advantages of the invention will become more apparent from the following detailed description of the invention when taken in conjunction with the accompanying drawings.

BRIEF DESCRIPTION OF THE DRAWINGS

FIG. 9 is a cross section showing the configuration of an image inspection device according to a fifth embodiment.

FIG. 10 is a cross section showing the configuration of an image inspection device according to a sixth embodiment.

DETAILED DESCRIPTION OF THE INVENTION

First Embodiment

Figure 1:
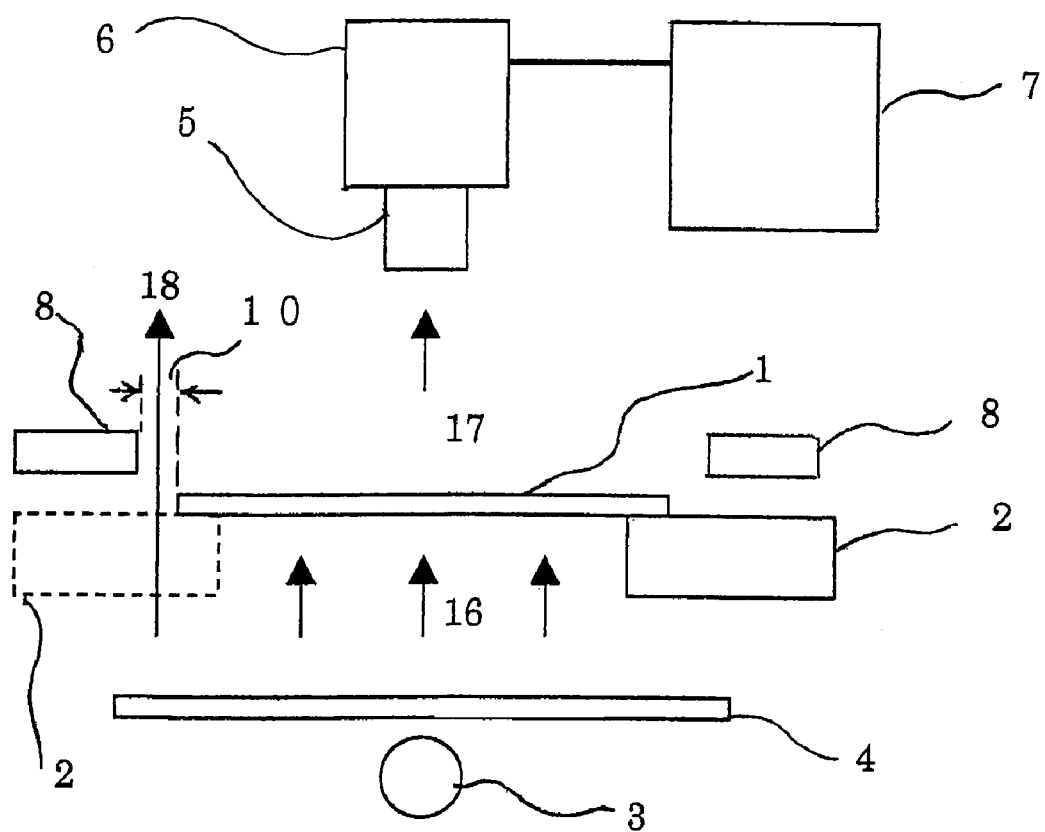
FIG. 1 is a cross section showing the configuration of an image inspection device according to a first embodiment of the invention.

FIG. 1 is a view of the side surface showing the configuration of an image inspection device according to a first embodiment of the invention. Referring to the drawing, a holder stand 2 (referred to as the inspection object hold means) to hold a semiconductor wafer 1 (inspection object) that transmits infrared rays is provided on the lower side of the semiconductor wafer 1 so as to hold the semiconductor wafer 1 horizontally. Herein, descriptions will be given in a case where the outer shape of the semiconductor wafer 1 is a rectangle by way of example. An infrared light source 3 that irradiates infrared rays to an upper side is disposed below the semiconductor wafer 1, and a plate of an infrared diffusing medium 4 that diffuses infrared rays is provided above the infrared light source 3. The infrared diffusing medium 4 is furnished with a function of diffusing infrared rays homogeneously, and it is, for example, a translucent or frosted glass plate. Infrared rays after coming out from the infrared diffusing medium 4 and before going incident on the semiconductor wafer 1 are denoted by reference numeral 16 for ease of description. Infrared rays having passed through the semiconductor wafer 1 are denoted by reference numeral 17. A camera 6 (hereinafter, referred to as the infrared camera or infrared light camera) equipped with an infrared lens 5 and sensitive to infrared rays is disposed above the semiconductor wafer 1. A video signal imaged by the infrared camera 6 is displayed on a monitor 7, and the inspector detects a defect through a visual inspection. Alternatively, a defect is detected automatically from an image using unillustrated image processing means. A mask 8 (referred to as the mask means) that blocks infrared rays leaking from the outer side of the semiconductor wafer 1 is provided around the semiconductor wafer 1 at the same height.

Figure 2A:
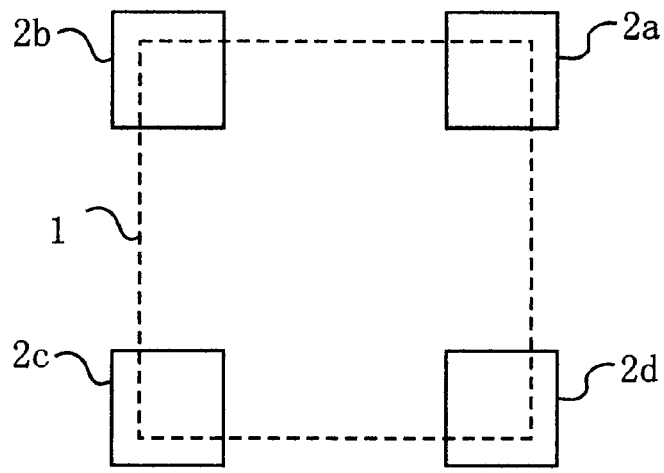
FIG. 2 is an explanatory view used to describe operations of the image inspection device of FIG. 1.
Figure 2B:
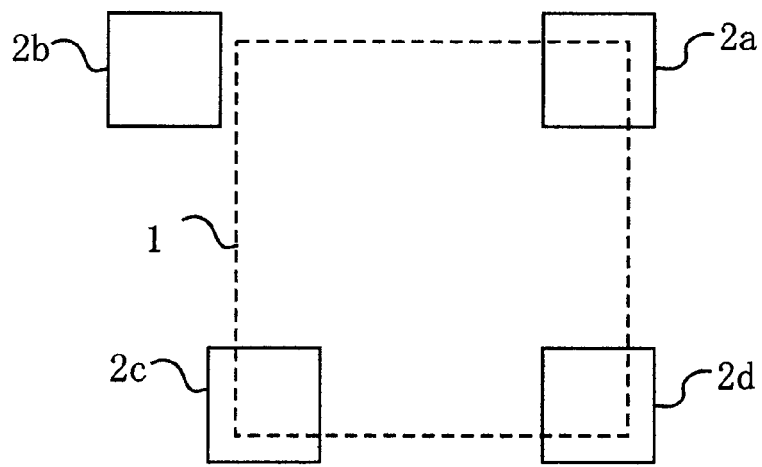
Figure 2C:
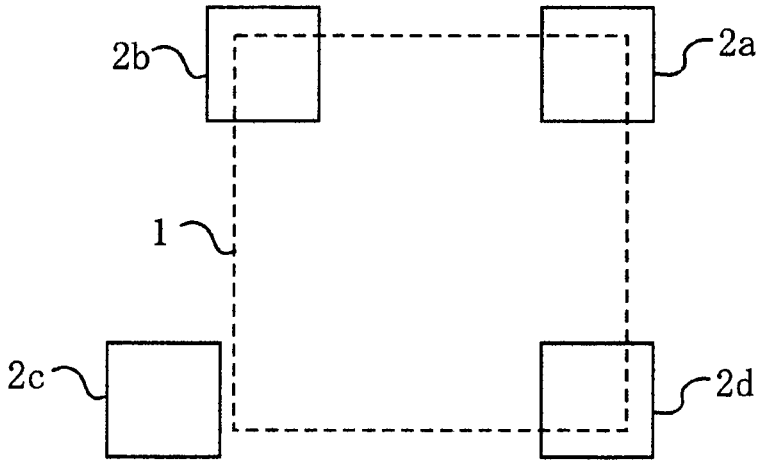

FIG. 2 is a view used to describe the basic configuration and operation of the holder stand (inspection object hold means) 2. As are shown in FIG. 2a, FIG. 2b, and FIG. 2c, the holder stand 2 includes four support means 2a through 2d. These support means have a structure such that allows each to evacuate in a direction almost parallel to the surface of the semiconductor wafer 1 up to a position not to cover the plate surface of the semiconductor wafer 1 by an unillustrated slider (referred to as the evacuater means). More specifically, FIG. 2a is a view showing a state where none of them has evacuated. FIG. 2b is a view showing a state where the support stands 2b and 2d have evacuated. FIG. 2c is a view showing a state where the support stands 2a and 2c have evacuated.

Operations will now be described. Infrared rays emitted from the infrared light source 3 are made homogeneous in a direction parallel to the surface of the semiconductor wafer by the infrared diffusing medium 4, and the infrared rays 16 that have been made homogeneous are irradiated to the semiconductor wafer from the back surface of the semiconductor wafer 1 (from the lower side facing the drawing). The semiconductor wafer 1 is positioned relatively with respect to the position of the infrared camera 6 by an unillustrated positioning mechanism and then held by the support stands 2a and 2c (referred to as the first support means) at the opposing corners as is shown in FIG. 2b. In this instance, the support stands 2b and 2d have evacuated to positions so as not to overlap the semiconductor wafer 1. The irradiated infrared rays 16 pass through the inside of the semiconductor wafer to the main surface and further to the outside. The transmitted infrared rays 17 are captured in the infrared camera 6 by the infrared lens 5, and the monitor 7 displays an image signal outputted from the infrared camera in the form of an image that can be visually confirmed, so that an individual conducts an inspection for a crack by watching this image. It goes without saying that an inspection may be conducted automatically using an image processing device having stored unillustrated image inspection software instead of using the monitor 7. Subsequently, the support stands 2b and 2d are returned to the original positions as is shown in FIG. 2a. Then, as is shown in FIG. 2c, after the semiconductor wafer 1 is held by the support stands 2b and 2d (referred to as the second support means) at the other opposing corners, the support stands 2a and 2c are moved to evacuate to positions so as not to overlap the semiconductor wafer 1. The transmitted infrared rays 17 are captured in the infrared camera 6 in the same procedure as the procedure described above for an image to be displayed on the monitor 7. This enables an inspection of the image to be conducted at the portion where an inspection could not be performed last because the support stands 2a and 2c overlapped the semiconductor wafer 1.

Figure 3:
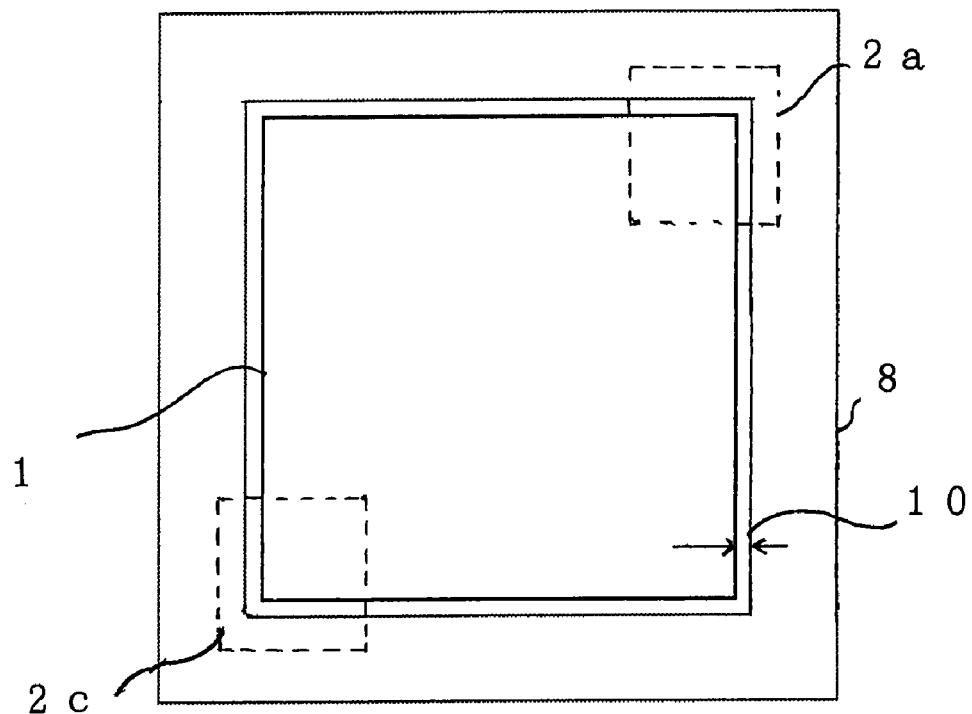
FIG. 3 is a view used to describe detailed portions in the configuration of the image inspection device of FIG. 1.
Figure 4:
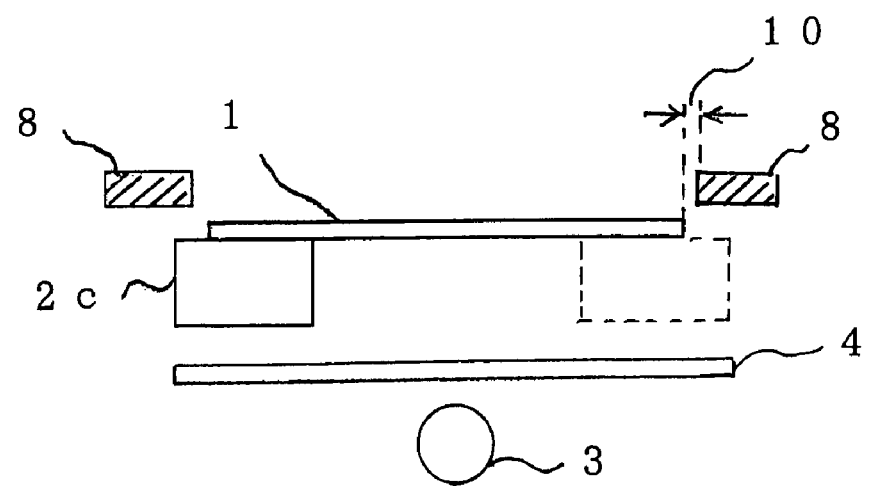
FIG. 4 is a side view of FIG. 3.

As are shown in a top view of FIG. 3 and a side view of FIG. 4, the mask 8 is provided while securing a slight clearance 10 for light to pass through the peripheral portion of the semiconductor wafer 1. In a case where the clearance 10 is large, too much light 18 passes through the clearing 10 when an image of the peripheral portion of the semiconductor wafer 1 is taken by the infrared camera 6, which gives rise to halation. It thus becomes impossible to distinguish a crack from a normal portion. When the width of the clearance 10 is as small as 0.2 to 1.0 mm, and preferably about 0.5 mm, light 18 passing through the clearance 10 does not cause halation, and a satisfactory image can be obtained even at the peripheral portion of the semiconductor wafer 1. It should be noted that the narrower the width of the clearance becomes, the less the light leaks, which causes, however, the holder stand 2 to come into contact with the semiconductor wafer 1 more frequently, and the semiconductor wafer 1 may possibly become dirty through useless contact. The size specified above is therefore chosen as a trade-off between leakage and contact. Consequently, it becomes possible to detect a difference in a transmission state of infrared rays between a crack and a normal portion even at the peripheral portion of the semiconductor wafer 1, which enables an inspection for a crack to be conducted across the entire surface.

Figure 5:
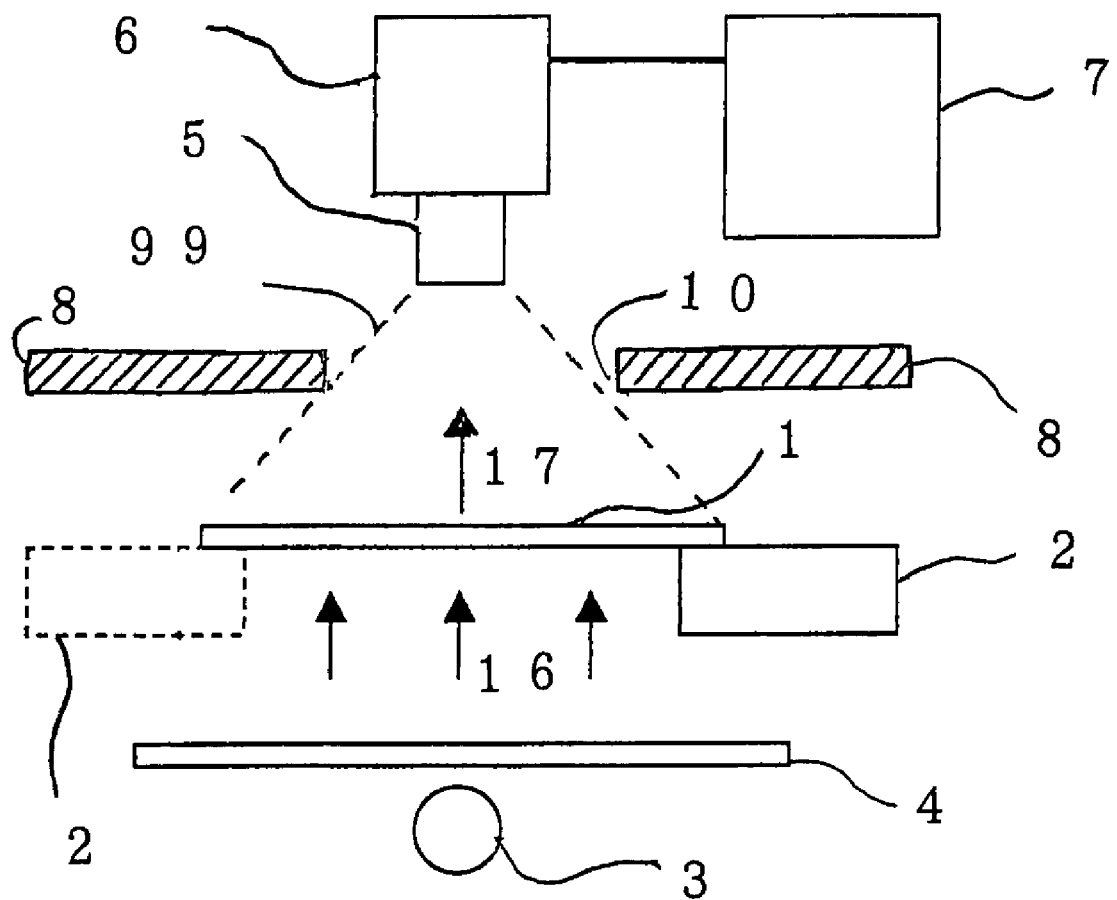
FIG. 5 is a cross section showing the configuration of an image inspection device according to a second embodiment.

A description was given by illustrating the mask 8 at the same height as the semiconductor wafer 1 in FIG. 1. However, it may be provided at any of the following positions: between the semiconductor wafer 1 and the infrared lens 5, almost just beside the semiconductor wafer 1, and between the semiconductor wafer 1 and the infrared light source 3. It should be noted that in a case where the mask 8 is provided between the semiconductor wafer 1 and the infrared lens 5 as is shown in FIG. 5, it is possible to avoid interference with the positioning mechanism and the holder stand of the semiconductor wafer 1, which in turn makes it possible to provide an inexpensive inspection device using a simpler mechanism. In this case, however, it is preferable to make the size of the mask 8 smaller in response to the apparent size (explanatory line 99 in the drawing) when the inspection object 1 is viewed from the camera lens 5. In other words, the size is set so that the clearance 10 between the explanation line 99 in the drawing and the mask 8 takes a value that falls within the range specified above. To be more specific, mask means is provided so as to shield the inspection object from infrared rays while securing a clearance of 0.2 to 1.0 mm on the outer side of the angle of field when the inspection object is viewed from the infrared camera. In addition, because there are a problem that the contour of the portion shielded by the mask 8 becomes blur as the mask 8 comes into closer proximity to the camera lens 5 and a problem that halation occurs more readily as the mask 8 is spaced apart farther from the inspection object 1, it is preferable that a distance of the mask 8 from the inspection object 1 falls within the range of focal depth of the camera lens 5, for example, about 0.2 to 1.0 mm.

The infrared diffusing medium 4 provided between the semiconductor wafer 1 and the infrared light source 3 enables an inspection for a crack to be conducted in a more reliable manner by making it easier to prevent halation by diffusing infrared rays. It can also protect the infrared light source 3 by preventing dirt, pieces of the semiconductor wafer 1, or the like from falling directly onto the infrared light source 3.

Of the descriptions above, the procedure to conduct an inspection will be described again stepwise in an organized manner.

Initially, a plate-shaped inspection object that transmits infrared rays is supported on the first support means.

Infrared rays are irradiated to the inspection object from one surface thereof.

The mask means for shielding the inspection object from the infrared rays is provided around the inspection object (it may be provided in advance).

Infrared rays having passed through the inspection object at the portion uncovered with the first support means are imaged by the infrared camera provided on the other surface of the inspection object for an inspection to be conducted.

After the inspection object is supported on the second support means, the first support means is evacuated to the position so as not to shield the inspection subject.

Infrared rays having passed through the inspection object at the portion uncovered with the second support means are imaged by the infrared camera for an inspection to be conducted. It goes without saying that the imaging range in this instance includes a range that was not imaged when an image was taken while the inspection object was supported on the first support means.

Second Embodiment

Figure 6:
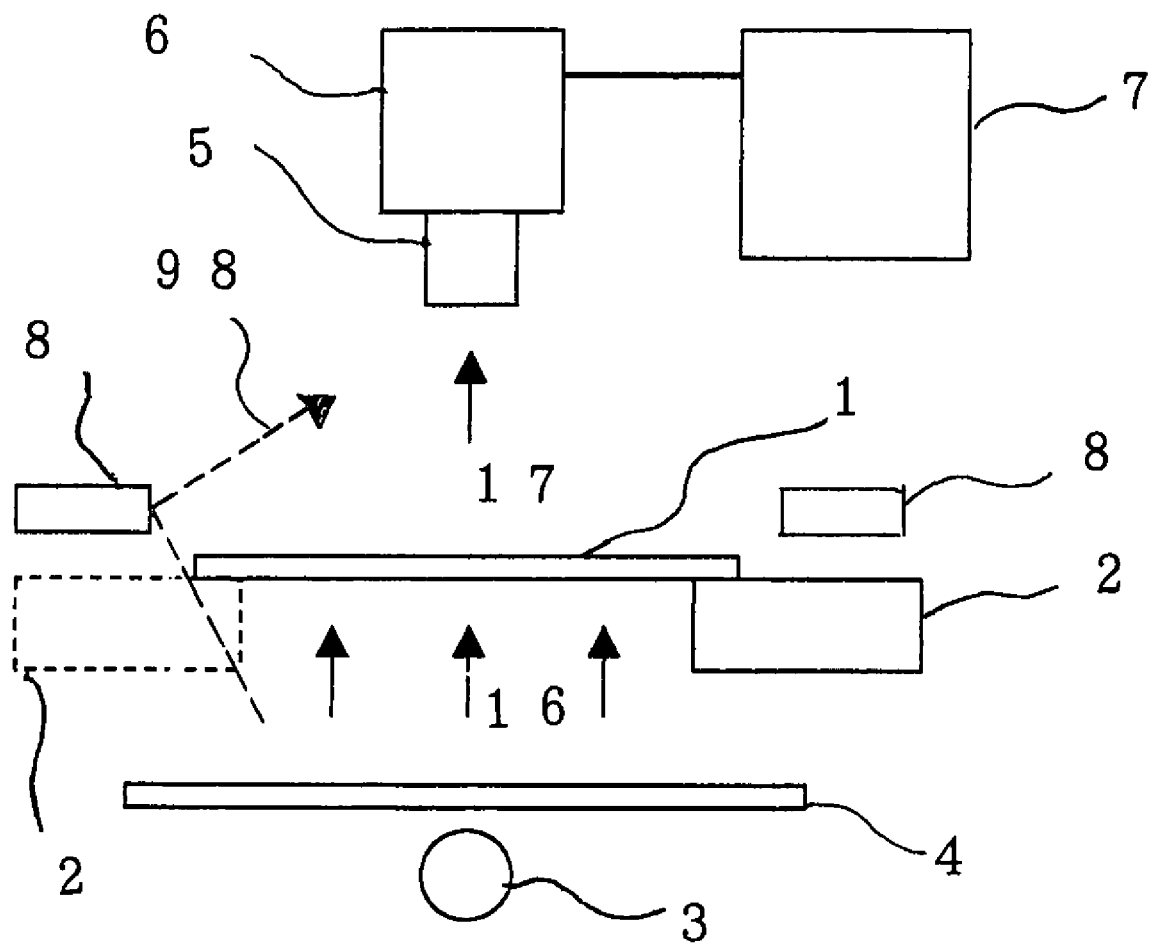
FIG. 6 is a view used to describe an image inspection device according to a third embodiment.
Figure 7:
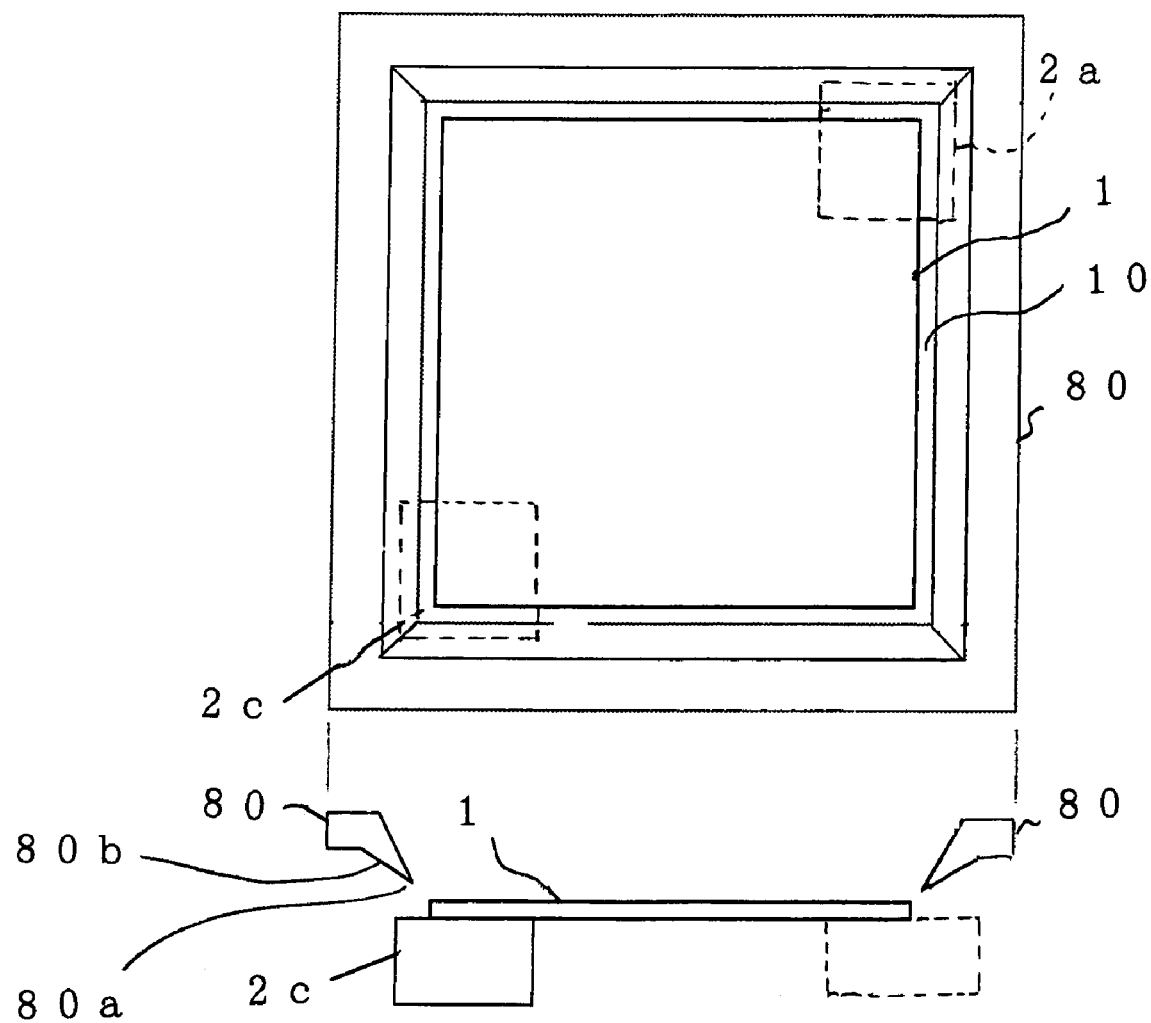
FIG. 7 is a view showing detailed portions of the image inspection device according to the third embodiment.

In FIG. 1 of the first embodiment, the mask 8 is illustrated as a thick plate-shaped member. However, as is shown in FIG. 6, because the end faces of the plate of the mask 8 are present at the position that can be viewed from the camera 6, light coming out from a translucent object 4 may possibly be reflected on the end faces (reflected light is denoted by 98 in the drawing) to come into the camera. In order to solve this problem, as is shown in FIG. 7, a non-reflecting mask 80 is used herein, which is structured to have sharp edges 80*a* formed in a thin and sharply pointed shape as the end faces and inclined portions 80*b*, so that extra light will not be reflected in a direction toward the semiconductor wafer 1 and the infrared camera 6. Because the sharp edges 80*a* are too thin for light to be reflected, no reflected light goes into the camera. In addition, the inclined portions 80*b* prevent extra reflected light from reaching the camera. It is thus possible to obtain a more satisfactory image, which enables an inspection for a crack to be conducted in a more stable manner. It is preferable to configure in such a manner that the thickness of the sharp edges 80*a* at the end portion is, for example, 0.2 mm or less, or an angle of, for example, 10° to 80° is given to the inclined portions 80*b* with respect to the surface of the semiconductor wafer so that light reflected on the inclined portions will not go inside the semiconductor wafer 1.

Third Embodiment

Figure 8:
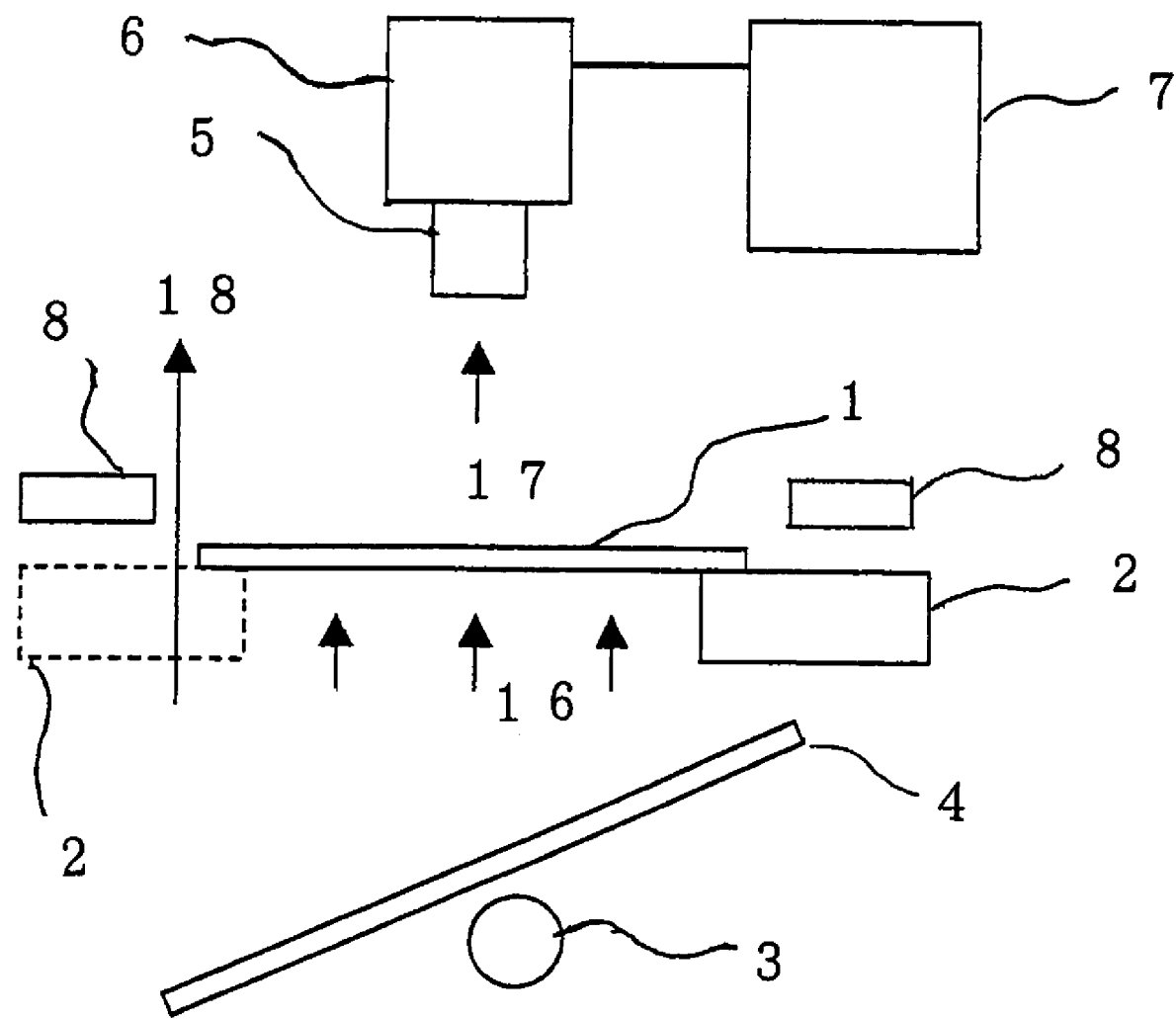
FIG. 8 is a cross section showing the configuration of an image inspection device according to a fourth embodiment.

The first embodiment and the second embodiment have described a case where the infrared diffusing medium 4 is provided horizontally. However, as is shown in FIG. 8, the infrared diffusing medium 4 may be provided at a specific angle, for example, an angle of 5° to 60° with respect to the horizontal level. By providing the infrared diffusing medium 4 at a specific angle, it is possible to prevent dirt, pieces of the semiconductor wafer, or the like from deposing on the infrared diffusing medium 4. This prevents dirt, pieces or the like accumulating on the top surface of the translucent object 4 from showing up in an image taken by the infrared camera 6. Hence, by eliminating a false recognition of a crack, it is possible to conduct an inspection for a crack in a more stable manner.

Fourth Embodiment

Referring to FIG. 1 of the first embodiment, the hold means 2 was described that it is moved by the unillustrated slider (evacuater means) in parallel with the surface of the semiconductor wafer 1. However, the evacuater means is not limited to the one as described above as long as it has a structure to allow the hold means 2 to evacuate to a position not to overlap the semiconductor wafer 1 (not to cover the surface of the semiconductor wafer). For example, the support stands 2*a* through 2*d* may be evacuated to positions so as not to overlap the semiconductor wafer 1 by a rotation mechanism that rotates about a support point 97 as is shown in FIG. 9.

Fifth Embodiment

FIG. 10 is a view showing the configuration of a fifth embodiment of the invention. Descriptions are omitted for those labeled with the same reference numerals with respect to FIG. 1 because they are the same or equivalent portions, and descriptions will be given in detail in the point that the semiconductor wafer 1 is supported on a glass plate 9 that transmits infrared rays, which is different from the first embodiment.

In the first embodiment, in order to inspect the peripheral portion of the semiconductor wafer 1, it is necessary to switch the support stands 2a through 2d between the stands used to support the semiconductor wafer 1 during imaging and the stands to be evacuated during imaging. However, as is shown in FIG. 10, by configuring to support the wafer 1 using the fixed transparent (transparent for infrared rays) glass plate 9 instead of using the hold stand of FIG. 1, it is possible to inspect the semiconductor wafer 1 across the entire surface at a time. Hence, a time needed for an inspection can be shorter, and the mechanism to make the hold stand movable can be omitted. It is therefore possible to provide a more efficient and inexpensive inspection device. The glass plate 9 transparent for infrared rays is the light-transmitting hold means referred to in this invention.

When the mask 8 is provided at the same height as the semiconductor wafer 1 as in the first embodiment, it is provided while securing a slight clearance 10 for light to pass through the peripheral portion of the semiconductor wafer 1. In a case where the width of the clearance 10 is large, too much light 18 passes through the clearing 10 when an image of the peripheral portion of the semiconductor wafer 1 is taken by the infrared camera 6, which gives rise to halation. It thus becomes impossible to distinguish a crack from a normal portion. When the clearance 10 is as small as 0.2 to 1 mm, and preferably about 0.5 mm, light 18 passing through the clearance 10 does not cause halation, and a satisfactory image can be obtained at the peripheral portion of the semiconductor wafer 1. Consequently, it becomes possible to detect a difference in a transmission state of infrared rays between a crack and a normal portion, which enables an inspection for a crack to be conducted even at the peripheral portion of the semiconductor wafer 1.

In addition, as in the first embodiment, the mask 8 may be provided in any of the following positions: between the semiconductor wafer 1 and the infrared camera 6, almost just beside the semiconductor wafer 1, and between the semiconductor wafer 1 and the infrared light source 3. It should be noted that in a case where the mask 8 is provided between the semiconductor wafer 1 and the infrared camera 6, it is possible to avoid interference with the positioning mechanism of the semiconductor wafer and the glass plate, which in turn makes it possible to provide an inexpensive inspection device using a simpler mechanism.

Alternatively, as in the second embodiment, the mask 8 may be the non-reflecting mask 80 so as not to reflect extra light in a direction toward the semiconductor wafer 1 and the infrared camera 6. Reflection of light can be eliminated by providing the inclined portions to the end portions of the support stands, which in turn makes it possible to obtain a more satisfactory image. It is thus possible to conduct an inspection for a crack in a more stable manner.

A case where the infrared diffusing medium 4 is provided horizontally is shown in the drawing. However, as is shown in the fourth embodiment, the infrared diffusing medium 4 may be provided at a specific angle. By providing the infrared diffusing medium 4 at a specific angle, dirt, pieces of the semiconductor wafer, or the like will not deposit on the infrared diffusing medium 4. It is thus possible to prevent dirt, pieces, or the like from showing up in an image taken by the infrared camera. Hence, by eliminating a false recognition of a crack, it is possible to conduct an inspection for a crack in a more stable manner.

The light-transmitting hold means 9 comes into contact with the semiconductor wafer 1. However, because the light-transmitting hold means per se is inspected together with the semiconductor wafer 1, the presence of dirt is found immediately. The light-transmitting hold means is therefore used always in a clean state, which eliminates the risk of making the semiconductor wafer dirty.

Sixth Embodiment

FIG. 10 of the fifth embodiment shows a case where the glass plate 9 to hold the semiconductor wafer 1 and the infrared diffusing medium 4 that makes infrared rays homogeneous are provided separately. The invention, however, is not limited to this configuration, and the infrared diffusing medium 4 may hold the semiconductor wafer 1. In short, the infrared diffusing medium 4 may also serve as the glass plate 9 that supports the semiconductor wafer 1. By adopting this configuration, it is possible to provide an inexpensive inspection device using a simpler mechanism.

Seventh Embodiment

Figure 11:
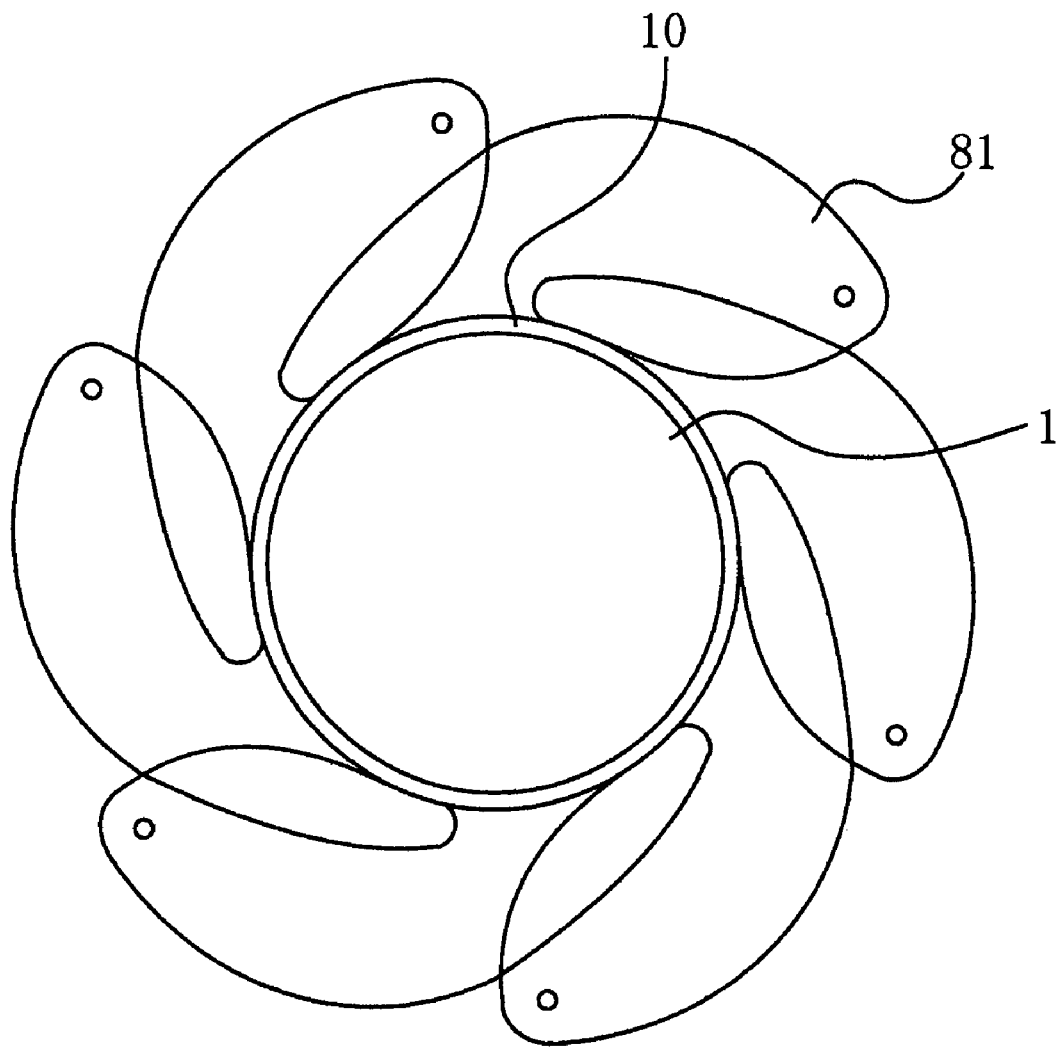
FIG. 11 is a view showing the structure of detailed portions of an image inspection device according to a seventh embodiment.

In the description of each embodiment above, the semiconductor wafer 1 was described and illustrated as having a rectangular shape. However, some semiconductor wafers generally manufactured are of a circular shape. Even when the semiconductor wafer is of a circular shape, the principle underlying each embedment can be applied directly. For example, it is possible to secure a clearance having the width of 0.2 to 1 mm with the use of a mask having the structure similar to that of the mechanical aperture mechanism in a camera like an aperture mask 81 shown in FIG. 11. More specifically, it is configured in such a manner that plural infrared shielding blades are provided to overlap one on another in a rotatable manner respectively around plural rotational shafts disposed on a circle, and the diameter of the hole at the center can be varied by changing the angel of rotation. The shape of such a mechanical aperture mechanism is well known, and detailed description thereof is omitted herein. It goes without saying, however, that the aperture mechanism mask is usable for a circular inspection object in all the embodiments described above.

In the description of each embodiment above, the inspection object was described as the semiconductor wafer 1. However, it is not limited to a semiconductor wafer as long as it is an inspection object that transmits infrared rays. It goes without saying that an inspection can be conducted, for example, for a liquid crystal panel or the front panel of a solar battery.

The image inspection device of the invention can be used not only for an inspection of a semiconductor wafer, but also for an inspection of a panel plate of a liquid crystal display and a solar battery panel.

Various modifications and alterations of this invention will be apparent to those skilled in the art without departing from the scope and spirit of this invention, and it should be understood that this is not limited to the illustrative embodiments set forth herein.

What is claimed is:

1. An image inspection method comprising:
    supporting almost horizontally a plate-shaped inspection object having a property of transmitting infrared rays with a first support means in a first position relative to the inspection object;

irradiating the inspection object on a first surface thereof with infrared rays;

shielding the inspection object from at least some of the infrared rays by providing a mask means around an outer side of the inspection object within a plane that is substantially the same as a plate surface of the inspection object;

imaging infrared rays that have passed through the inspection object at a portion uncovered by the first support means by obtaining an image with an infrared camera provided adjacent to a second surface of the inspection object opposite to the first surface, and inspecting the image;

supporting the inspection object with second support means at a second position relative to the inspection object that is different from the first position of the first support means, and then moving the first support means to a position in which the first support means does not shield the inspection object; and imaging infrared rays that have passed through the inspection object at a portion uncovered by the second support means by obtaining an image with the infrared camera, and inspecting the image.

2. The image inspection method according to claim 1, wherein:

the inspection object is a semiconductor wafer.

3. An image inspection device comprising:

an infrared light source that is adapted to irradiate with infrared rays a first surface of a plate-shaped inspection object having a property of transmitting infrared rays and provided almost horizontally;

an infrared camera disposed near a second surface of the inspection object, and adapted to image the infrared rays having passed through the inspection object by obtaining an image thereof;

mask means for shielding the inspection object from the infrared rays disposed while securing a specific clearance from an end face of the plate-shaped inspection object, disposed near an outer side of the inspection object within a plane substantially the same as the plane of a surface of the inspection object; and inspection object holding means having support means for supporting the inspection object at a first position, having a first support means for supporting the inspection object, a second support means for supporting the inspection object at a second position different from the first position, and evacuater means for evacuating the first support means to a position that does not cover a surface of the inspection object.

4. The image inspection device according to claim 3, wherein:

the support means of the inspection object hold means is formed of a glass plate capable of transmitting the infrared rays.

5. The image inspection device according to claim 4, wherein:

the support means formed of the glass plate is provided between the infrared light source and the inspection object, and also serves as an infrared diffusing medium that diffuses the infrared rays.

6. The image inspection device according to claim 3, wherein:

the specific clearance between the mask means and the end face of the inspection object is 0.2 to 1 mm.

7. The image inspection device according to claim 3, wherein:

the mask means has a sharp edge provided at a position opposing the end face of the inspection object and an inclined portion that reflects infrared rays emitted from the infrared light source to a side where the inspection object is absent.

8. The image inspection device according to claim 3, further comprising:

an infrared diffusing medium provided between the infrared light source and the inspection object to diffuse the infrared light.

9. The image inspection device according to claim 8, wherein:

the infrared diffusing medium is provided at an angle of 5° to 60° with respect to a horizontal surface.

10. The image inspection device according to claim 3, wherein:

the inspection object is shaped like a circular plate, and the mask means is configured to provide plural infrared shielding blades that overlap one on another in a rotatable manner around plural rotational axes disposed on a circle.

11. The image inspection device according to claim 3, wherein:

the inspection object is a semiconductor wafer.

12. An image inspection device comprising:

an infrared light source;

an infrared camera disposed opposite the infrared light source;

an inspection object holder stand, disposed between the infrared light source and the infrared camera, and having:

a first support, adapted to support an inspection object at a first position;

a second support, adapted to support the inspection object at a second position different from the first position; and an evacuater, adapted to evacuate at least the first support to a position such that, after evacuation, the first support does not block the path of infrared light between a first surface of the inspection object and the infrared light source, and does not block the path of infrared light between a second surface of the inspection object and the infrared camera.

13. The image inspection device according to claim 12, further comprising a mask, disposed between the infrared light source and the infrared camera, and adapted to provide a specific clearance from an end face of the inspection object.

14. The image inspection device according to claim 13, wherein the specific clearance between the mask and the end face of the inspection object ranges from 0.2 to 1 mm.

15. The image inspection device according to claim 13, wherein the mask has plural infrared shielding blades that are rotatable around plural rotational axes disposed on a circle, such that the infrared shielding blades can be rotated to overlap one another.

16. The image inspection device according to claim 13, wherein the mask is disposed adjacent to the inspection object holder.

17. The image inspection device according to claim 13, wherein the mask is disposed between the inspection object holder and the infrared light source.

18. The image inspection device according to claim 13, wherein the mask is disposed between the inspection object holder and the infrared camera.

\* \* \* \* \*